United States Patent [19]

Reher et al.

[11] Patent Number: 4,957,550

[45] Date of Patent: Sep. 18, 1990

[54] ULTRASONIC MACHINING TOOL FOR MACHINING ORTHODONTIC BRACKETS

[75] Inventors: James F. Reher, Pomona; Farrokh Farzin-Nia, Inglewood, both of Calif.

[73] Assignee: Manufacturers Hanover Trust Co., New York, N.Y.

[21] Appl. No.: 239,320

[22] Filed: Sep. 1, 1988

Related U.S. Application Data

[62] Division of Ser. No. 046,430, May 6, 1987, Pat. No. 4,838,786.

[51] Int. Cl.⁵ ............................................. B22F 9/00
[52] U.S. Cl. ...................................... 75/246; 75/243; 420/36; 51/59 SS
[58] Field of Search ................... 420/11, 12, 15, 27, 420/34, 36, 38, 43, 55, 95, 97, 100; 75/242, 243, 246; 51/59 SS

[56] References Cited

U.S. PATENT DOCUMENTS

| | | | |
|---|---|---|---|
| 1,322,511 | 11/1919 | Armstrong | 420/11 |
| 1,522,813 | 1/1925 | Etchells | 420/55 |
| 1,542,233 | 6/1925 | Girin | 420/55 |
| 2,990,275 | 6/1961 | Binder et al. | 75/126 |
| 3,340,048 | 9/1967 | Floreen | 75/128 |
| 3,502,462 | 3/1970 | Dabkowski et al. | 75/128 |
| 3,516,824 | 6/1970 | Gottlieb et al. | 75/128 |
| 3,627,514 | 12/1971 | Steven | 75/126 |
| 3,834,901 | 9/1974 | Kamiya et al. | 75/128 |
| 4,100,701 | 7/1978 | Bessaguet | 51/157 |
| 4,343,111 | 8/1982 | Inoue | 51/59 SS |
| 4,576,642 | 3/1986 | Holtz, Jr. | 75/239 |
| 4,616,447 | 10/1986 | Haas et al. | 51/59 SS |
| 4,822,567 | 4/1989 | Kato et al. | 420/95 |

Primary Examiner—Stephen J. Lechert, Jr.
Assistant Examiner—Leon Nigohosian, Jr.
Attorney, Agent, or Firm—Marjama & Pincelli

[57] ABSTRACT

An orthodontic bracket and method of making same wherein the bracket has at least one tiewing integrally formed with a base portion. In one form of the invention the bracket is provided with at least one longitudinally extending groove which extends into the base portion, the groove having at least a portion extending beyond at a least a portion of the groove opening. In another aspect of the present invention is directed to a method of making an orthodontic bracket using ultrasonic machining techniques.

1 Claim, 8 Drawing Sheets

TO HORN

ULTRASONIC MACHINING TOOL FOR MACHINING ORTHODONTIC BRACKETS

This is a Divisional of application Ser. No. 046,430 filed on May 6, 1987, now U.S. Pat. No. 4,838,786.

This invention relates to an orthodontic bracket and to a method for making an orthodontic bracket.

BACKGROUND OF THE INVENTION

Orthodontic brackets have long been used for applying corrective forces to teeth. Typically an orthodontic bracket comprises a tooth bonding surface and a slot for receiving an archwire which transmits corrective forces from the archwire to the tooth. Generally, orthodontic brackets of the prior art are made of a metal so as to provide sufficient strength for the transmission of these forces to the teeth. An individual undergoing orthodontic treatment generally has a considerable number of these brackets applied to his or her teeth. Individuals generally consider these orthodontic brackets as being extremely unsightly in appearance.

It is long considered desirable by manufacturers of orthodontic brackets to provide a bracket which is less sightly in appearance. One solution suggested was the use of clear plastic materials, however, these materials have been found to have insufficient strength for transmitting the appropriate forces to the teeth. In order to avoid this problem metal supports or inserts have been suggested for use with plastic. However, this then suffers from the same unsightly problem that total metal brackets present, however, maybe now to a certain lesser degree.

There has also been suggested use of single crystalline alumina material for an orthodontic bracket as described in U.S. Pat. No. 4,639,218 to Jones et al. and U.S. Pat. No. 4,595,598 to DeLuca et al. In U.S. Pat. No. 4,639,218 there is described an alpha alumina orthodontic bracket which is made by a seed crystal which is pulled from molten alumina by a die having a cross-sectional configuration substantially identical to that of the orthodontic bracket. After the crystal is drawn it forms a rod which is cut into a plurality of individual brackets by known cutting/grinding techniques. A problem with this type of method is that it is relatively expensive and is limited to the configurations that may be applied to the top surface of the bracket. Additionally, and perhaps more importantly, the grinding and cutting technique used to form the final configuration results in sharp edges which may cause damage to the tissue and introduce stresses in the product which may later cause failure of the bracket.

Another problem associated with orthodontic brackets made of single crystalline material, also recognized by the '218 reference, is the ability of the material to adhere to the surface of a tooth. The '598 reference to De Luca et al. discloses two ways whereby adhesion is improved between the bracket and tooth. In one method a small undercut is provided at each side edge of the bonding base. A problem with this method is that it requires a grinding operation which can introduce serious surface flaws to the very brittle crystalline material.

In the second method a siliceous layer is applied to the bracket and then a silicone coupling agent is applied to the bracket which has an affinity for the siliceous material. A problem associated with this method is that great care is required in placing of the siliceous layer on the bracket and applying the cement. Any contaminations on any of the surfaces could substantially reduce the adhesion of the cement to the siliceous layer. Additionally, the shelf life of the coupling agent can have an adverse affect on the adhesive bond formed.

Applicants' have developed an improved orthodontic bracket and method of making same which minimizes or eliminates the problems of the prior art.

SUMMARY OF THE INVENTION

In one aspect of the invention there is provided an orthodontic bracket comprising at least one tiewing having a slot for receiving an archwire, a base portion integrally formed with the tiewing. The base portion having a surface for attachment to a tooth and having at least one longitudinally extending narrow groove across said bracket. The groove extending from the surface into the base portion and beyond at least a portion of the opening of the groove at said surface, said groove having no sharp edges of said base portion.

In another aspect of the invention a method of making an orthodontic bracket comprising the steps of providing a disc of desired material having a thickness substantially equal to the length of an orthodontic bracket; milling the cross-sectional profile of at least one bracket using ultrasonic machining.

DESCRIPTION OF THE PREFERRED EMBODIMENT

Figure 1:
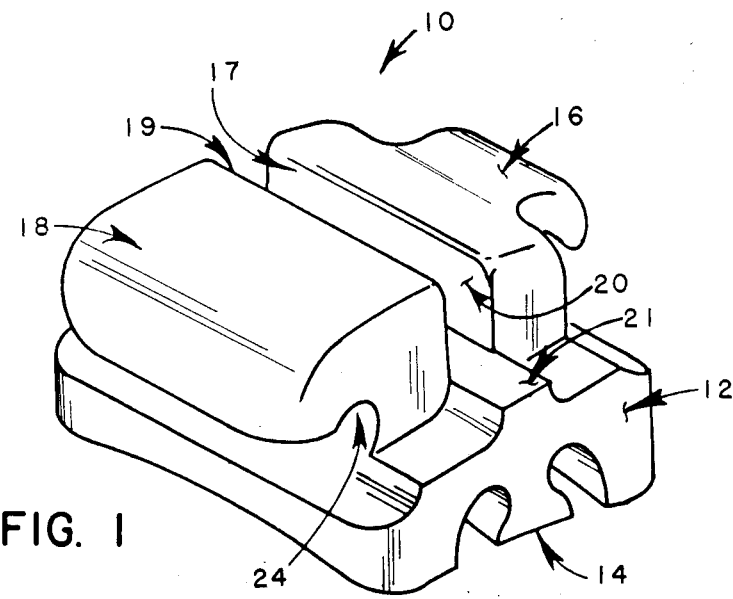
FIG. 1 is a perspective view of an orthodontic bracket made in accordance with the present invention.
Figure 4:
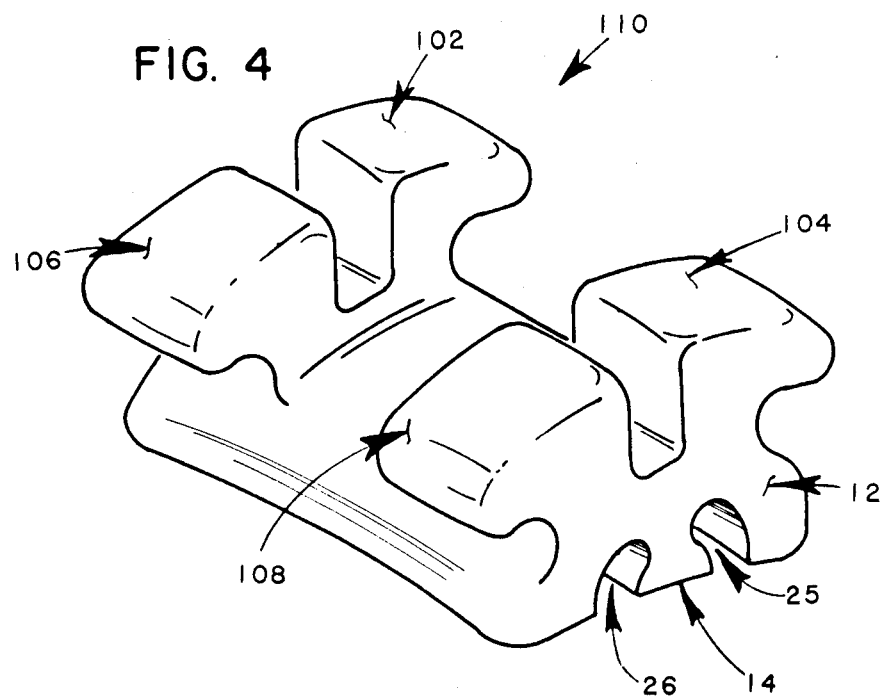
FIG. 4 is a perspective view of a modified orthodontic bracket made in accordance with the present invention.
Figure 2:
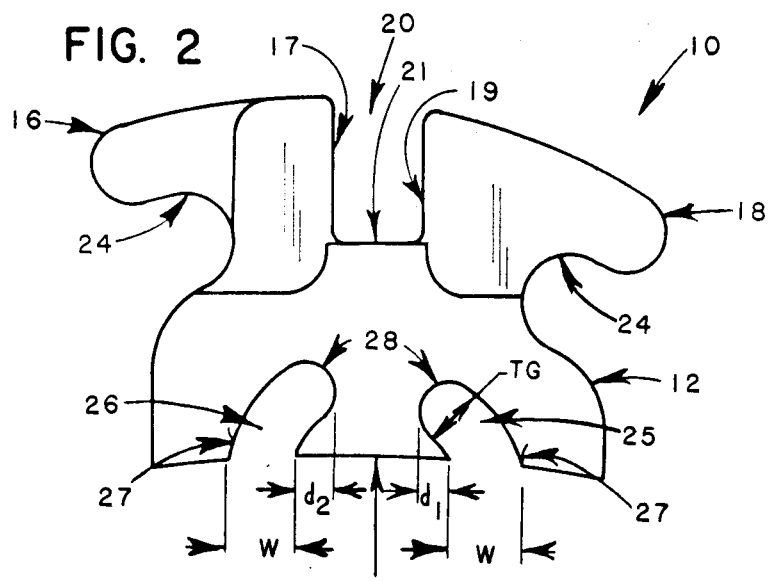
FIG. 2 is a side view of FIG. 1.
Figure 3:
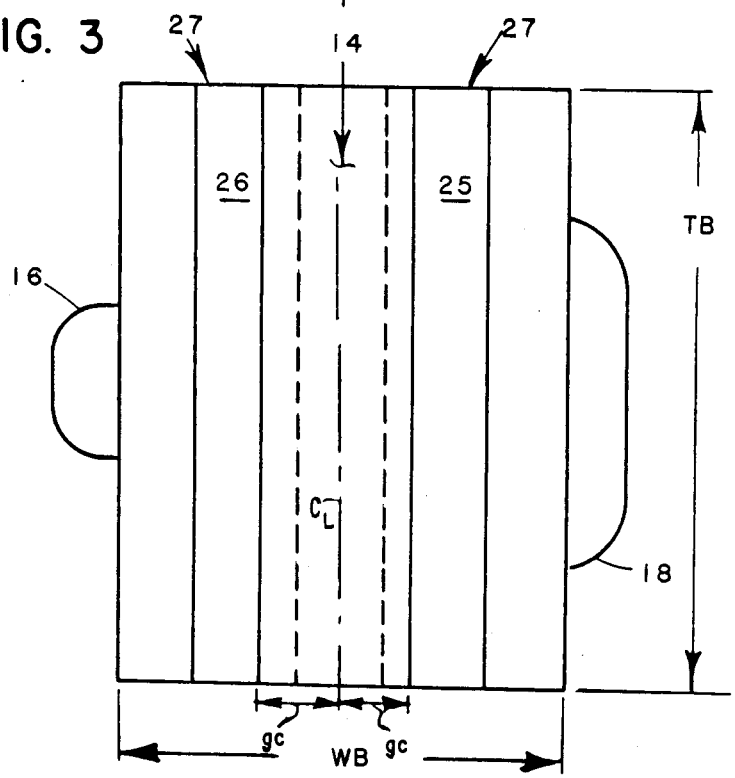
FIG. 3 is a bottom view of FIG. 1.

Referring to FIGS. 1, 2 and 3 there is illustrated an orthodontic bracket 10 made in accordance with the present invention. The bracket 10 is preferably made of a single crystal alumina material. In the particular embodiment illustrated the orthodontic bracket 10 is made of a alpha aluminum oxide purchase from Union Carbide under the trade name Linde Cz sapphire. The orthodontic bracket 10 has a base portion 12 having a bottom surface 14 which is bonded to the surface of a tooth. The bottom surface 14 having a length TB and width WB. Extending from the base portion is a single tiewing comprising an occlusal wing 18 and a gingival wing 16, each having a slot defining surface 17, 19, respectively, which forms an archwire slot 20 therebetween for receiving an archwire. The bottom surface 21 of slot 20 is provided with a platform for rotational control of the archwire. In the particular embodiment illustrated occlusal wing 18 and gingival wing 16 are each provided a recess 24 for receiving an elastomeric o-ring which is used to maintain the archwire (not shown) in slot 20. However, it is to be understood that the archwire may be secured to the bracket in any known or desired manner. Additionally the bracket 10 is not limited to a single tiewing construction as illustrated in FIG. 1. Referring to FIG. 4 there is illustrated a bracket 110 similar to bracket 10, like numeral indicating identical parts. Instead of a single tiewing bracket 110 has a pair of gingival tiewings 102, 104 and a pair of occlusal tiewings 106, 108.

Referring back to FIGS. 1, 2 and 3 base portion 12 is provided with a pair of longitudinal extending undercut narrow grooves 25, 26 which extend from the bottom surface 14 into base 12. The longitudinal axis of grooves 25, 26 is preferably substantially parallel to the occlusal plane of a patient and substantially equally spaced from longitudinal center line CL of bracket 10 a distance GD. The grooves 25, 26 each have a width W at the opening on bottom surface 14. The grooves 25, 26 extend into base portion 12 such that the groove extends a distance d1, d2, respectively beyond the opening 27 of grooves 25, 26 at bottom surface 14. In the particular embodiment illustrated W is about 0.015", d1 and d2 is about 0.01". The distance that grooves 25, 26 extend into base 12 may vary in accordance to the desired amount of torque that is to be applied to the bracket. For a zero degree torque bracket, the length grooves 25. 26 will preferably be substantially equally. Depending upon the amount of torque being applied to the bracket and bracket placement, this will be determinative of the distance grooves 25, 26 extends into base portion 12. Generally the higher the torque, the greater the differences grooves 25, 26 extend into base portion 12. The maximum differences in the amount of grooves 25, 26 extends into base portion 12 will occur at a torque angle of about 22°. In the particular embodiment the groove 25 associated with the gingival wing 18 extends further into base portion 12 than groove 26. Accordingly d1 would be greater than d2. The grooves 25, 26 may take a variety of shapes and configurations as desired so long as it does not substantially offset the structural integrity of the bracket. In this regard it is preferred that no cross-sectional thickness of the bracket 10 be less than about 0.025".

The bracket 10 is bonded to a tooth by the use of a lightly filled cement which is placed onto bottom surface 14 and into grooves 26. The undercut grooves 26 provides a means for mechanically interlocking the bonding cement to the bracket. The grooves 25, 26 are preferably designed so as to not have any sharp edges internally thereof, so as to avoid any potential surface flaws. In the particular embodiment illustrated the inner ends 28 have a substantially semi-circular configuration. Preferably, as illustrated, the grooves 25, 26 have a substantially uniform cross-sectional thickness TG about its length.

Figure 5:
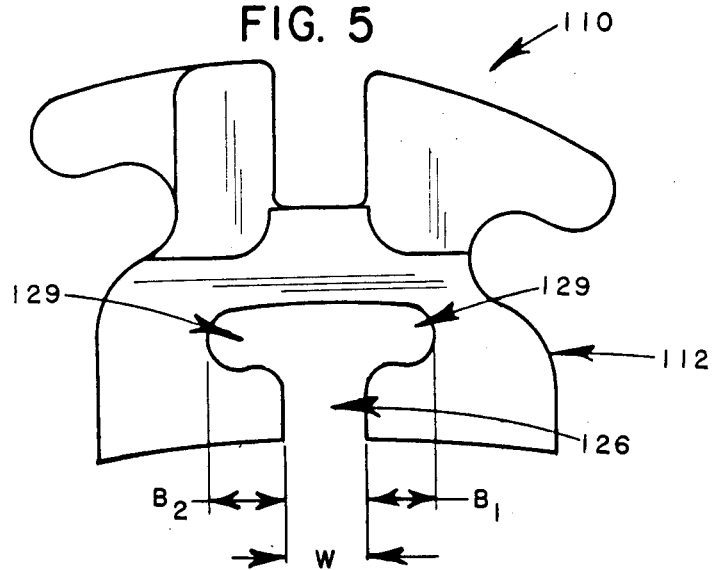
FIG. 5 is a side view of yet another modified orthodontic bracket made in accordance with the present invention.

In the preferred embodiment illustrated in FIGS. 1–3 there is illustrated two grooves 25, 26 which extend into the base portion 12. However, the present invention is not so limited. For example, referring to FIG. 5 there is illustrated a bracket 110 made in accordance with the present invention having a single groove 126. The groove 126 has a single opening 127 having a width W similar to grooves 25, 26 of bracket 10. The groove 126 extends into base portion 112 and has two branches 129 which extend in opposite directions. Each of the branches 129 extend beyond the groove opening 127 a distance B1, B2, respectively. Yet still, a bracket made in accordance with the present invention may be provided with more than two grooves may be provided if desired so long as they don't interfere with the structural integrity of the bracket.

Figure 5A:
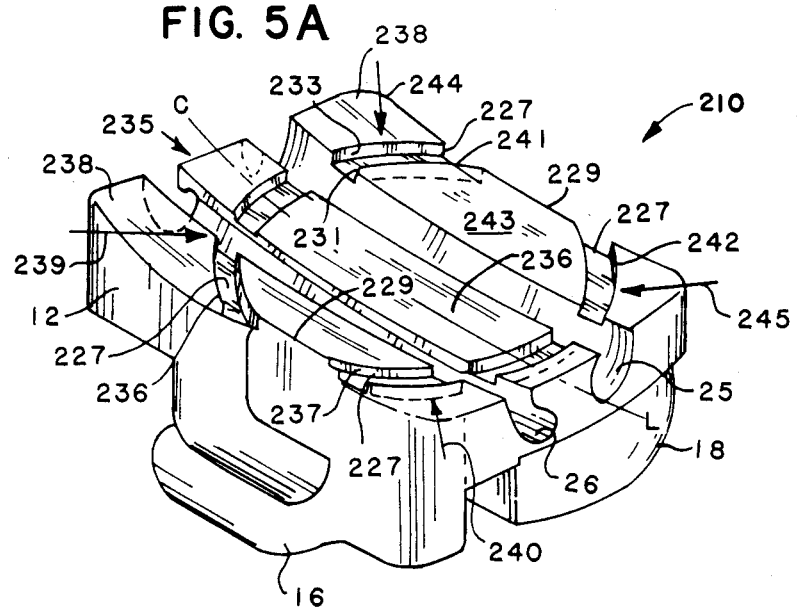
FIG. 5A is a bottom perspective view of another modified bracket made in accordance with the present invention.

Referring to FIG. 5A there is illustrated a bottom perspective view of another modified bracket 210 made in accordance with the present invention. Bracket 210 is similar to bracket 10, like numerals indicating indentical part, except that an additional substantial circular groove 227 is provided in base portion 12 by a pair of oppositely spaced straight side walls 231, 233. As can be seen, the groove 227 extends past the side edges 229 of the bracket 210, however, the present invention is not so limited, as the 227 may be entirely in base portion 12 if so desired. The groove 227 assists in primarily resisting shear forces in the direction which grooves 25, 26 are weak in resisting. The central 234 portion of groove 227 in central portion 236 of base portion 12 primarily resist shear forces in the axial direction parallel to the center line CL as indicated by arrow 235. The portions 236, 237 of groove 227 in side portions 238, resist shear forces in the diagonal direction as indicated by arrows 239, 240 respectively. Whereas the portions 241, 242 of groove 227 in side portion 243 of base 12 primarily resist shear force in the diagonal directions indicated by arrows 244, 245 respectively. Since longitudinal grooves 25, 26 are provided, shear forces in a direction perpendicular to center axis CL are primarily handled by these grooves. Therefore groove 227 does not require groove portions to resist these forces. Accordingly there is no need to provide the entire circular groove with base portion 12.

While FIG. 5A illustrates a substantially circular 227 groove, base portion 12 may be provided with substantially straight grooves in portions, 234, 238, 243 (not shown). Preferably at least one groove is provided in each portion 238 and 243 which extend at an angle in the range of about 30° to about 60° with respect to center line CL, generally at an angle of 45°. At least one groove in each portion lieing in the opposite direction, e.g., direction indicated by arrows 238 and 244.

The function of the undercut grooves 25, 26 is to provide a means for a mechanical interlock between the orthodontic bracket and tooth. Single crystal alumina characteristically exhibits a high surface energy, accordingly it is, therefore, extremely difficult to adhesively bond a bracket made of this material to a tooth. A mechanical interlock is desirable so as to improve the adhesion of the bracket to the tooth. While chemical treatments and surface coatings may provide adequate bonding strengths, the approach of a mechanical interlock such as stainless mesh commonly used in the prior, has been shown to yield the highest bonding strength and durability. In order to assure adaption of the bracket bonding base 12 to the tooth anatomy, the bottom surface 14 is preferably provided with compound radii.

Further improvements to bonding is possible through secondary surface treatments to surface 14 so as to increase the mechanical interlock between the bracket and tooth. The mechanical interlock of these secondary surface treatments is believed to occur at a microscopic level, whereby grooves 25, 26 provides a mechanical interlock function on a macroscopic level.

Figure 6:
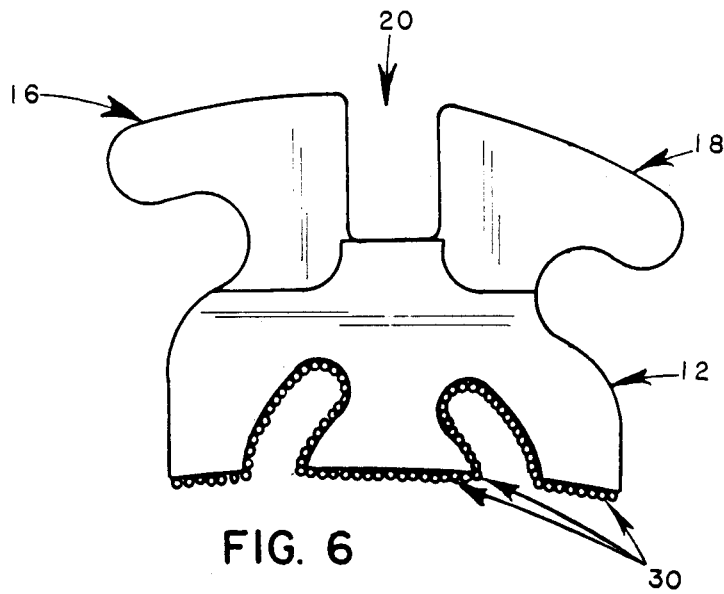
FIG. 6 is a side view of FIG. 1 illustrating a diagrammatical representation of a treatment to the bonding base thereof.

There are various forms of surface treatments and coatings possible which will now be discussed. One such treatment is the providing of alumina particle texturing to the surface 14. This particular form of surface treatment is schematically illustrated in FIG. 6. Alumina particles 30 ranging in size from 0.03 to 1 $\mu$m (microns) are attached to the surface 14 of the bonding base 12 by a combined brazing/sintering operation. The particle 30 in FIG. 6 has been greatly enlarged solely for the purpose of illustration. This process is accomplished by first placing alumina particles 30 on a thin glass film which is sandwiched between two release films. One side of the glass film is provided with a tacky binder. The release films used are of a particular weight and texture which is conducive to chopping (cutting) operations. The glass film is then chopped into individual pieces which has the same shape of the bonding surface 14. The release film on the side of the glass which does not have alumina particles is removed. The remaining glass alumina laminate is then placed on the bonding base surface 14 of bracket 10 and then subjected to a brazing/sintering operation a temperature between approximately 520° to 650° Centigrade for about 30 minutes in an air atmosphere. The function of the glass film is to primarily serve as a braze by which the alumina particles are attached to the surface 14. Subsequent to the brazing/sintering operation, a single alumina bracket 10 which posseses alumina particles/glass bond and base coating is then placed in a hydrofluoric acid etch solution. The hydrofluoric etch generates a second level of microscopic bonding base. The etch removes a majority of the glass braze which was used to attach the aluminum particles to the bonding base 14. During the etching process, the removal of glass roughens the surface of whatever glass remains The resulting bonding base 14 then posseses essentially three levels of bonding base which function on a microscopic and macroscopic levels of mechanical interlock. The preferred glass is a combination of oxides of boron, sodium, potassium and silicone which has a silica concentration no greater than 20 percent by weight.

A second treatment to surface 14 comprises an alkaline etch. Single crystal alumina has been shown to be slightly soluable in a strong alkaline solution This limited soluability allows a single crystal alumina surface 14 to be etched, thus establish a microscopic level of mechanical interlock. In addition to improving the mechanical interlock between the bracket and tooth the alkaline etch may also provide improved bonding between the cement and the bracket.

A third treatment comprises a leachable glass coating. Soda-lime and alumina silicate glasses are soluable in dilute acidic solutions as well as strong alkaline solutions. A film made of such glass is sandwiched between release films can be used in the same manner as set forth in the alumina particle texturing procedures described above. That is, individual pieces of glass film are chopped (cut) in the shape of bottom surface 14. The release film is removed with the glass film being placed on the surface 14. The glass/bracket is then subjected to glazing operation at 530°-1200° Centigrade in an air atmosphere. A bracket 10 is then placed in an acid or alkaline solution Such solutions preferably dissolve components of the glass. The dissolution of these components result in a porous network of glass which is attached to the bonding base. Existance of such a porous network and interpenetrating pores leads to a microscopic form of a mechanical interlock.

Crystal alumina bracket 10 as disclosed in the present invention is very sensitive to surface flaws. As such it is extremely important in the manufacturing of such bracket that the number of surface flaws be minimized. Applicants have found that a single crystal alumina brackets which are fabricated using ultrasonic machining techniques provides an improved feature not possible using conventional machining, cutting and grinding techniques which typically use a diamond cutting tool. Ultrasonic machining process is a well known technique.

Applicants have found that a single crystal alumina bracket made using a diamond cutting tool had a RMS surface roughness of 500 micro inch (0.0005). This was in contrast to a single crystal alumina bracket made using ultrasonic techniques which had a RMS surface roughness of 200 micro inch (0.0002). The ultrasonic machining process clearly providing significantly smaller surface flaws thereby minimizing material failure. Another significant advantage of using ultrasonic machining is that sharp edges or corners may be entirely avoided as illustrated in the preferred embodiment. The presence of sharp edges or corners produce stress concentration areas. Accordingly ultrasonic machining offers the advantage of minimizing or eliminating these stress concentration areas by providing a bracket having substantially no sharp edges or corners either internally of any grooves or recesses or on the external surface of the bracket.

Figure 7:
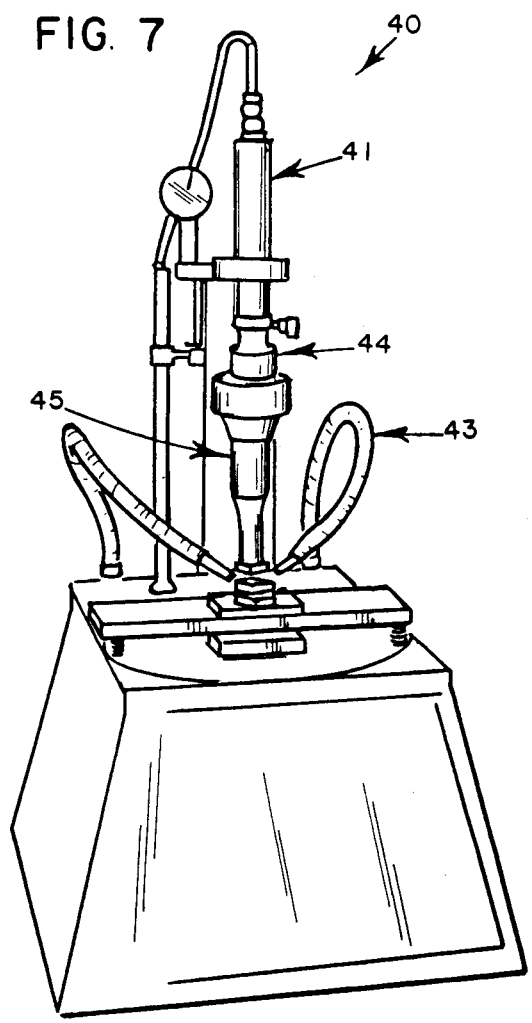
FIG. 7 is a perspective view of an ultrasonic apparatus used to make the orthodontic bracket of FIG. 1.
Figure 8:
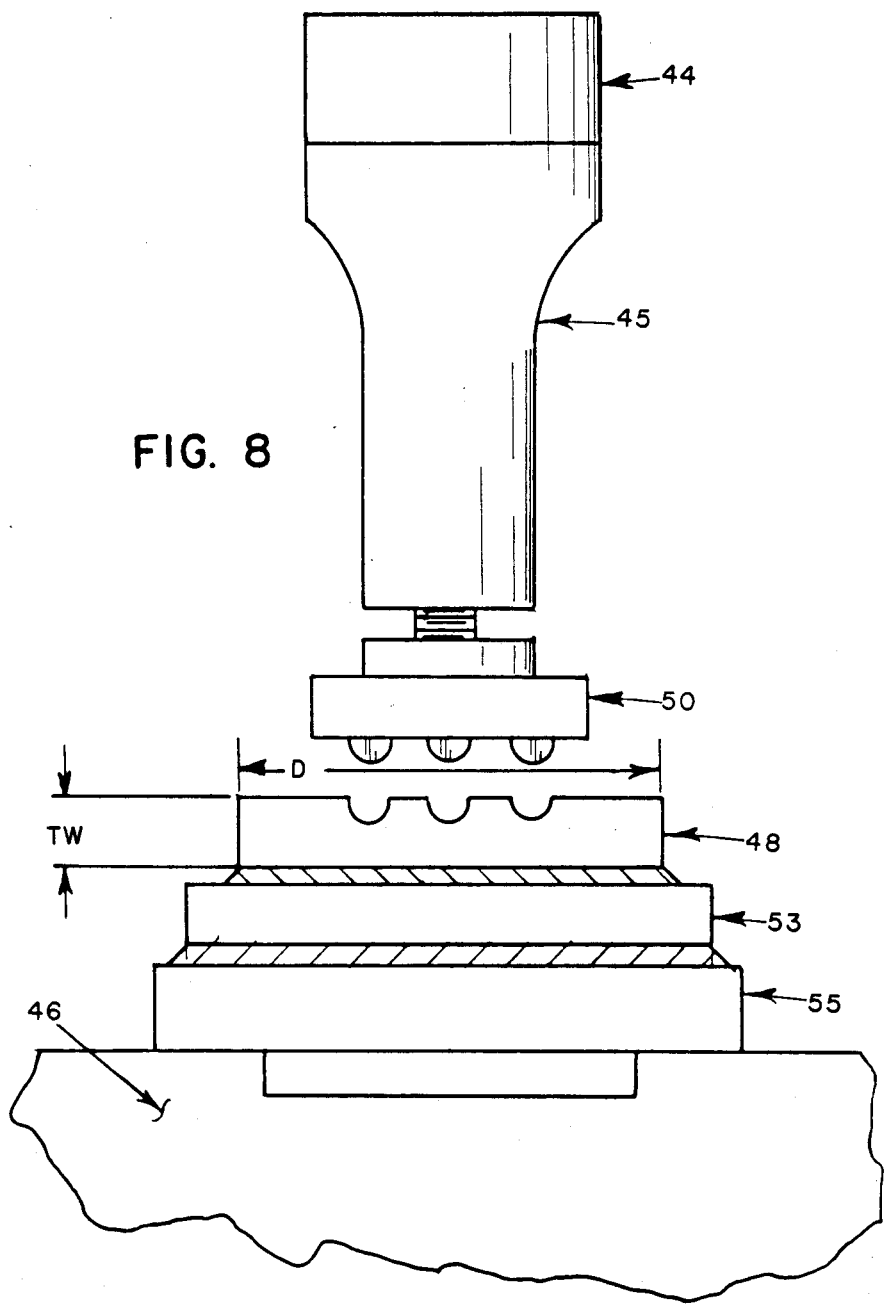
FIG. 8 is an enlarged fragmentary view of FIG. 7 illustrating a work piece being machined.

Referring to FIGS. 7 and 8 there is illustrated a typical apparatus 40 used to conduct ultrasonic machining. Ultrasonic machining comprises the converting of line voltage to a high frequency electrical energy by a power supply converter. This energy is provided to a piezoelectric converter 41.

The ultrasonic apparatus 40 comprises essentially six basic components; a piezoelectric converter 41, a coupler 44, an abrasive slurry pumping system (43), a milling platform 46, an ultrasonic horn 45 and a power source and controller (not shown). The power source converts the conventional power line voltage to 20,000 hz electrical high frequency energy. This energy is provided to converter 41, which transforms electrical energy into mechanical motion. The mechanical motion of the converter is amplified and transmitted to the horn 45 by coupler 44. A cutting tool 50 is attached to horn 45 either by brazing or mechanical means. In the particular embodiment illustrated tool 50 is attached to horn 45 by threaded means, i.e., the tool 50 is threaded into horn 45. The horn 45 and tool 50 are caused to vibrate perpendicular to the tool surface thousands of times per second with no side to side motion. The resulting action causes a shape contained by the tool to be reproduced in the work piece 48.

The ultrasonic machining process is performed by a cutting tool 45 which osciliates at a high frequency, typically 20,000 cycles per minute in an abrasive slurry, usually boron carbide or silicone carbide particles suspended in a liquid medium, such as water, between the vibrating tool surface and the work piece 46. The abrasive particles strike the work piece 46 at a force equal to approximately 150,000 times their own weight. These tiny abrasive particles chip off microscopic bites and grind a counterpart of the tool surface. Using ultrasonic machining, the work material is not stressed, distorted or heated because the grinding force is seldom over 10 pounds. There is never any direct tool to work piece contact in the presence of a cool slurry which makes this a cold cutting process. This is to be distinguished from a prior art diamond cutting or grinding operations which introduce substantially greater stresses and surface flaws to the work piece. The shape of the tool 50 corresponds to the shape to be produced in the work piece. The high speed reciprocations of the tool 50 drives the abrasive material in the slurry across a small gap (generally a few thousands of an inch) against the work piece 48 as illustrated in FIG. 8. The impact of the abrasive is the energy which is principally responsible for the material removed from the work piece 48. The abrasive material typically used is boron or silicone carbide suspended in a liquid medium to form a slurry. Applicants have found that boron carbide having a grit size of 320 suspended in water provides suitable cutting.

Figure 9:
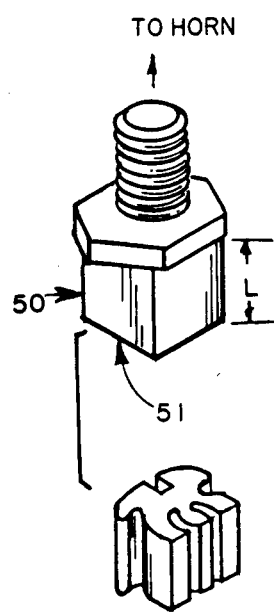
FIG. 9 is a perspective view of a tool used to make the initial profile cut on the work piece and an orthodontic bracket after the first cutting operation of the work piece.

In the particular application, the work piece 48 is a disc made of a single crystal alumina. The disc (work piece) is adhesively mounted to glass plate 53 which is mounted to a metal plate also by an adhesive. The plate 55 is typically held in position by an electromagnet in platform 46. The disc has a diameter D which in the particular embodiment is approximately 4 inches and a thickness TW of about 0.150 inches. The thickness TW is selected such that it equals the cross-sectional thickness of the thickness TB of the orthodontic bracket 10 (see FIG. 3). The basic profile of orthodontic bracket 10 is cut from the disc much in the same manner the cookie is cut from dough when using a cookie cutter. Accordingly, the first cut made in the disc is a profile cut of the orthodontic bracket. In order to effectively and efficiently use the tool a plurality of pieces are formed by a single tool. In the particular embodiment illustrated, the tool 45 produces approximately 72 individual cross-sectional profile cuts (called eaches) which are each made into an orthodontic bracket 10 (see FIGS. 9 and 12). Using a single tool 50 for production of multiple parts greatly enhances the economy of using ultrasonic machining in the production of the orthodontic brackets 10. This initial profile cut typically takes approximately an hour to produce the 72 parts. The tool 50 used to make the profile cut is relatively expensive due to its relatively complex configuration. Therefore the tool is preferably designed to used a plurality of times, before it is discarded. This is accomplished by providing tool 50 with a length L (see FIG. 9) so that after each profile cut, the cutting surface 51 may ground down so as to provide a fresh sharp clearn cutting surface 14. Due to the destructive nature of ultrasonic machining, the cutting surface 47 becomes worn to the point where it no longer provides a dimensionally accurate profile cut. Applicants have found that a tool having a length L of about one inch (2.54 cm) will provide a tool capable of making five profile cuts. After each profile cut the tool is ground down, for example, by a grinding wheel, to remove the warn portion of the tool. Typically about 0.2 inch is removed after each profile cut.

Figure 12:
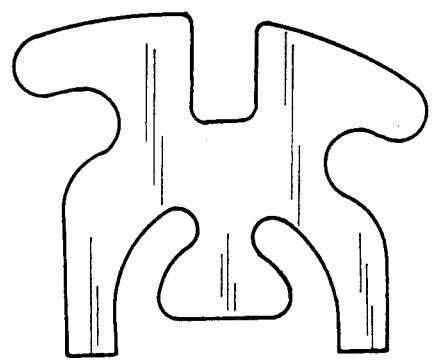
FIG. 12 is a side view of the bracket of FIG. 9.
Figure 13:
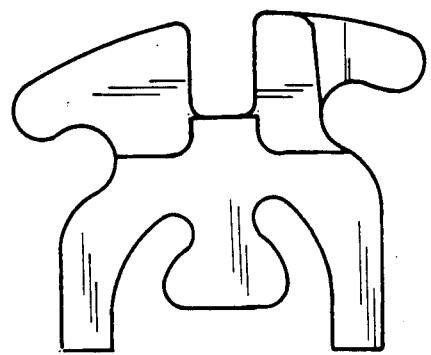
FIG. 13 is a side view of a modified bracket made in accordance with the present invention after a first initial profile cut has been made.
Figure 14:
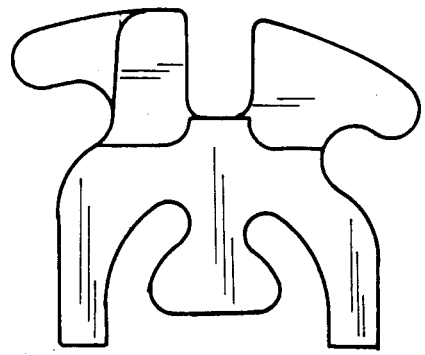
FIG. 14 is a side view of yet another modified bracket made in accordance with the present invention after a first profile cut has been made.

Referring to FIGS. 12, 13 and 14 there is illustrated various cross-sectional configurations of a bracket made in accordance with the present invention after an initial profile cut. As can be seen various cross-sectional configurations. The final configuration for surface 14 will be determined by the amount of torque required and which tooth the bracket will be used on as previously discussed.

Figure 10:
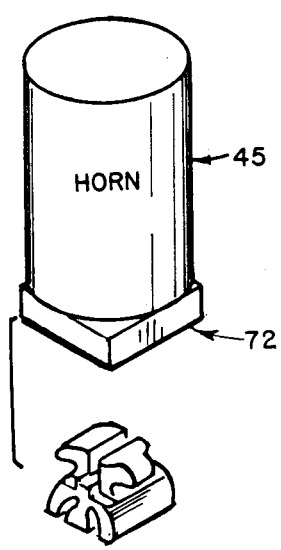
FIG. 10 is a perspective view of a tool used to make the top cut on the bracket of FIG. 9 and the bracket after the top cut has been made.
Figure 15:
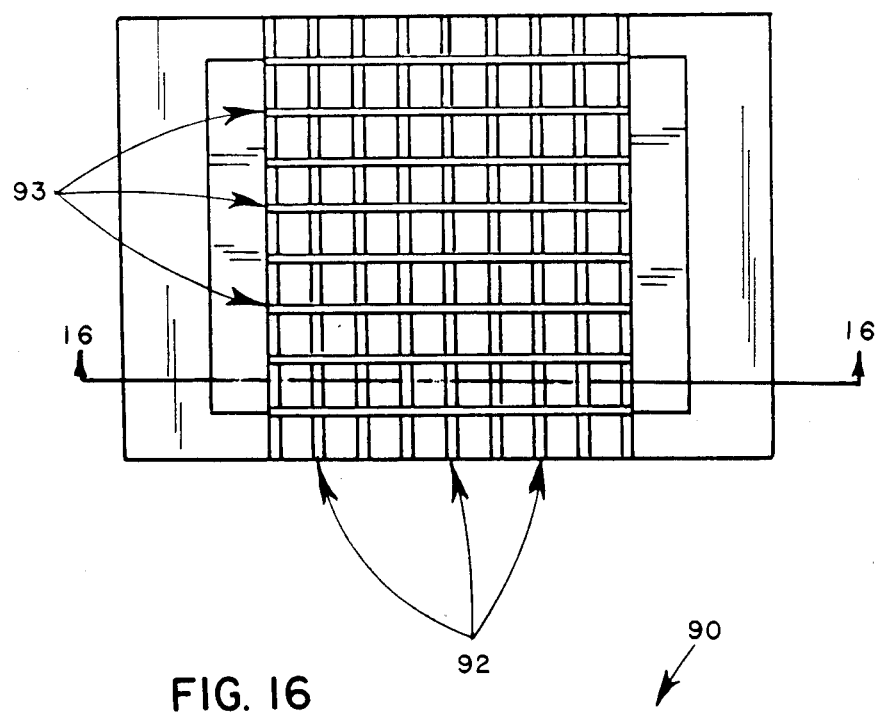
FIG. 15 is a top view of a tray used to hold a plurality of eaches during ultrasonic machining.
Figure 16:
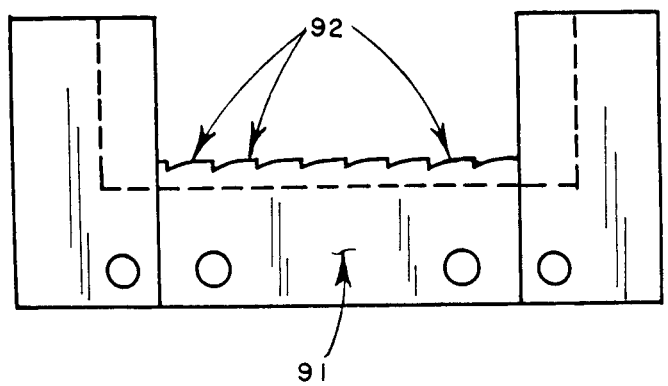
FIG. 16 is a cross-sectional view of the tray of FIG. 15 taken along line 16—16.

The eaches are then taken out, cleaned and placed in a fixture as shown in FIGS. 15 and 16 capable of holding a plurality of eaches. Typically the fixture or tray 90 which holds approximately 72 eaches. The tray 90 comprises of a base portion 91 having a plurality of spaced vertical projections 92 and a plurality of spaced horizontal projections 93 which form a plurality of seats 94, each seat 94 capable of holding in position a single eaches. In the particular embodiment illustrated the base of seat 94 is angled so as to allow the appropriate cut by the tool 50. The eaches are placed into individual seats 94 with the base down and are adhesively secured thereto. The tray 90 is appropriately placed in apparatus 40 beneath tool 45. A top cut, which forms the tiewings 16 and 18, is then produced by a top cutting tool 72 (see FIG. 10). The top cutting tool is also brazed onto the horn. During the top cut it can be seen that a bracket having a single pair of tiewings can be produced as illusrated in FIG. 1 or a pair of tiewings as shown in FIG. 4 may be produced. Typically this top cut takes approximately 10–15 minutes to complete. Top cut tool is used once and then discarded. The eaches are removed by applying an appropriate disolving agent.

It can be seen at this point that substantially the entire visual surface of the orthodontic bracket 10 is complete. The bracket at this point is removed and heat treated at a temperature in excess of approximately 1750° Centigrade for a preselected time period so as to substantially remove surface flaws that may have been produced.

Figure 11:
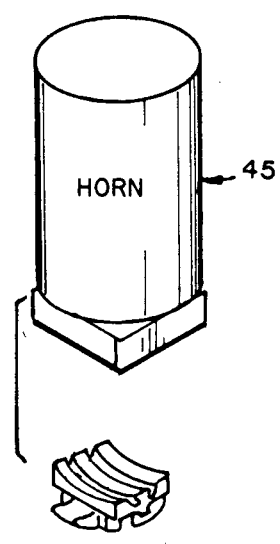
FIG. 11 is a perspective view of a tool used to make the bottom cut on the bracket of FIG. 10 and the bracket after the bottom cut has been made.

After this has been done, the eaches are then placed into another fixture (not shown) in the same manner as used in performing the top cut except that a mating projection is provided for mating with slot 20 formed in the top cut. However, it is understood that the top may be configured as desired so long as it holds in position the eaches during machinery. The eaches may also be adhesively attached to the tray in the same manner with tray 90 used for the top cut. A bottom cut tool (see FIG. 11) is attached to horn 45 for the bottom cut. The bottom cut usually takes about 10–15 minutes and is used only once before being discarded. Typically the bottom cut provides a compound radii to the bottom surface 14 so that it may conform substantially to the shape of the tooth. In addition the bottom cut can provide other grooves such as groove 227 illustrated in FIG. 5A. This procedure roughens the surface so as to improve the mechanical adhesion between the bracket and tooth. The bottom cut is preferably done after the heat treatment (annealing) previously discussed as the heat treatment reduces significantly the rougher surface for improved adhesion. However, if a rougher surface is not desired or needed the bottom cut may be conducted prior to the heat treatment.

Since the ultrasonic machine process is by its very nature a destructive method in which the cutting tools are consumed; it is preferred that an inexpensive, accurate and reliable method of tool manufacturing be used. Applicants have found that such tools 45 used in the ultrasonic machining process may be made by conventional powder metal compaction, power metal injection molded, investment casting or electric discharge machining.

All four methods have proven useful in the actual production of single crystal alumina orthodontic brackets. Each of these techniques permits the production of tools from conventional or custom metal alloys so as to minimize tool wear and provide the additional ability of providing process parameters which can be used to optimize the milling technique.

The conventional powder metal compaction technique has existed for many years. Typically this method involves the compaction of fine metal powders into the desired tool shape using punches and/or die sets. The powders typically used range in particle size no greater than 150 μm (microns) powders are generally elemental blends, comprising the desired alloy that usually have 0.5 to 1.0 percent lubricant. The powders are fed into the die set typically by a combination of gravity and vacuum. They are then pressed under great pressure to form a powder compact. Forces typically exerting during such pressing operations range from 180 to 220 KSI (kilo pounds per square inch). The combined action of the compaction forces and binder causes a green powder compact (greenware) to maintain its geometric integrity. Thus this enables a compact to be ejected from the die set and sent to the subsequent post compaction process steps, such as sintering. The greenware is then sintered under various atmospheric conditions and temperature ranges. The preferred alloy is a 50—50 weight percent blend of nickel and iron which is sintered in an atmosphere of dry hydrogen and nitrogen, at temperatures exceeding 2,000° F.

The powder metal injection molding is similar to that described for conventional powder metal compaction. The fundamental difference between the two processes include the method of introducing a feedstock to the molding cavity and basic composition of powder metal feedstock. Powder metal injection molding compound are usually elemental blends of powders ranging in size from 1 to 20 μm, possesing 10 percent organic binder by weight. The feedstock is fed into the molding cavity using conventional plastic injection molding equipment at temperatures ranging from 280°-300° F., at an injection pressure of about 1500 to 2000 psi. The combined action of organic binder and compaction pressure result in greenware, which is of sufficient density to allow for post molding operation, such as binder extraction and sintering. The preferred alloy is a preferred blend of 50 percent iron, 45 percent nickel and 5 percent tungston. The binder system used with the alloy consists of 30 percent polyethylene, 25 percent styrene butadiene rubber, with the balance being vegatable oil. The formulation of binder allows for an extraction scheme in which the styrene butadiene rubber and vegatable oil portions are extracted by trichloroethylene prior to sintering. This yield improvements in sintering efficiency, while maintaing greenware integrity since the polyethylene portion of the binder remains. Binder extraction is accomplished at 80° Centigrade in a recirculating bath of trichloroethylene. Optimal extraction occurs after four hours emersion in the extraction vessel. Subsequent to extraction, the trichloroethylene is allowed to evaporate from the molding tools. These tools are then sintered in an atmosphere of dry hydrogen in about 1300° Centigrade.

Investment casting involves the molding of plastic patterns which have the desired shape and pattern for the tool. The plastic patterns are then attached to a wax sprue in groups, preferably of six. The resultant plastic pattern/sprue assembly is then placed in a cylinder in which investment material is poured. Sufficient investment material is used so that the plastic patterns/sprue assembly is completely incapsulated. The resulting investment cylinder is then placed in an air furnace causing a wax sprue and plastic patterns to be burned out. The process results in plurality of molding cavities from which tools can be cast. The burned out investment cylinder is cleaned out and then prepared for the introduction of molten metal. Metal is heated to a molten state in a crucible and then poured into the investment cylinder. Upon cooling the investment material is broken away from the cast tool/sprue assembly. The cast tool is then removed from the sprue and is ready for usage. The preferred alloy is a 17-4 stainless steel. The preferred plastic for usage and formation of plastic patterns is polypropylene.

The fourth process for making tools is electric discharge machining. In general, the process involves the machining of a tool profile by placing electrically charged wire in close proximity of the work piece in the direction of a numerical controller. The work piece is moved toward the wire resulting in a machine cut. The control possible with electrical discharge machining permits for the machining of complex shape such as the profile of the orthodontic bracket 10. The preferred material for a tool manufacturing using this process is 17-4 stainless steel.

The tool used for the profile cut requires dimensional accuracy and is relatively complex in configuration. Accordingly it is preferred that the tool used for the profile cut be made using powder metal injection techniques. While investment casting may be used to produce such a tool, consistant quality and accuracy using this method is more difficult to maintain. Since the tools used for the top and bottom cuts are relatively simple in configuration conventional metalurgical technique and investment casting can provide relatively inexpensive and accurate tools which can be discarded after a single use. Applicants have found that tool used to form the profile cut preferably have a Rockwell hardness greater than 25 on the C scale. Tools having hardness substantially less than 25 are difficult to grind so as to provide a fresh surface.

Applicants have found a tool having the following composition by weight to work quite satisfactory (the nickel, chromium, cobalt and graphite portions being minimum amounts) for the profile cut.

| Nickel | 5 percent (minimum) |
|---|---|
| Chromium | 15 percent (minimum) |
| Cobalt | 3 percent (minimum) |
| Graphite | .05 percent (minimum) |
| Miscellaneous | .1 percent |
| Iron | balance. |

Tools used for the top and bottom cuts may be made of the following materials by weight:

| | |
|---|---|
| Nickel | 50 percent |
| Iron | 50 percent | or alternatively

| | |
|---|---|
| Cobalt | 30 percent |
| Iron | 70 percent |

It is to be understood that various other compositions, may be used for the tool 45 as is well known to those skilled in the art.

While the present invention is particularly adapted for use with hard single crystal sapphires materials, it is also applicable for use with other material, e.g., plastic, ceramics, and metals.

The ultrasonic milling technique disclosed herein allows for complex bracket configuration to relative easily made, especially without any sharp edges or corners. Various other profile configurations not illustrated may be made as well as other various top and bottom profiles may be made. For example, a substantially rhomboidal configuration can be imparted to the bracket as is described in U.S. Pat. No. 4,415,330.

Various other modifications may be made without departing from the scope of the present invention, the full scope of the present invention being described in the following claims.

What is claimed is:

1. A disposable ultrasonic machining tool for machining a plurality of orthodontic brackets at the same time, said tool being made of the following minimum materials by weight:

| | |
|---|---|
| Nickel | 5 percent (minimum) |
| Chromium | 15 percent (minimum) |
| Cobalt | 3 percent (minimum) |
| Graphite | .05 percent (minimum) |
| Miscellaneous | .1 percent |
| Iron | balance. |

* * * * *